US010866115B2

(12) United States Patent
Yuen et al.

(10) Patent No.: US 10,866,115 B2
(45) Date of Patent: Dec. 15, 2020

(54) DATA-FUSING ACTIVITY MONITORING DEVICE

(71) Applicant: Fitbit, Inc., San Francisco, CA (US)

(72) Inventors: Shelten Gee Jao Yuen, Berkeley, CA (US); Timothy M. Roberts, San Francisco, CA (US); Heiko Gernot Albert Panther, Oakland, CA (US); Barry Christopher Burton, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 73 days.

(21) Appl. No.: 16/195,094

(22) Filed: Nov. 19, 2018

(65) Prior Publication Data
US 2019/0186949 A1 Jun. 20, 2019

Related U.S. Application Data

(63) Continuation of application No. 14/713,288, filed on May 15, 2015, now Pat. No. 10,132,645, which is a
(Continued)

(51) Int. Cl.
*G01C 5/00* (2006.01)
*G01C 22/00* (2006.01)
(Continued)

(52) U.S. Cl.
CPC .......... *G01C 22/006* (2013.01); *A61B 5/1118* (2013.01); *A61B 5/1112* (2013.01); *A61B 5/6898* (2013.01)

(58) Field of Classification Search
CPC ....... G01C 22/006; G01C 5/00; A61B 5/1118; A61B 5/1112; A61B 5/6898
See application file for complete search history.

(56) References Cited

U.S. PATENT DOCUMENTS 4,312,358 A 1/1982 Barney
4,367,752 A 1/1983 Jimenez et al.
(Continued)

FOREIGN PATENT DOCUMENTS

JP 11347021 12/1999
WO WO 2012/170586 12/2012
(Continued)

OTHER PUBLICATIONS

U.S. Office Action dated Apr. 3, 2014, in U.S. Appl. No. 14/050,228.
(Continued)

*Primary Examiner* — Mohamed Charioui
(74) *Attorney, Agent, or Firm* — Weaver Austin Villeneuve & Sampson LLP

(57) ABSTRACT

An activity monitoring device accumulates a count of steps taken as an individual bearing the activity monitoring device travels by foot along a route, and wirelessly acquires positioning data from a discrete global-positioning device corresponding to a sequence of locations along the route. The activity monitoring device iteratively revises an estimated stride length of the individual based on the positioning data and the step count and iteratively updates a travel distance on a display of the activity monitoring device according to the step count and the estimated stride length as the individual proceeds from one location in the sequence to the next.

6 Claims, 5 Drawing Sheets

Related U.S. Application Data continuation of application No. 14/050,228, filed on Oct. 9, 2013, now Pat. No. 9,063,164.

(60) Provisional application No. 61/886,035, filed on Oct. 2, 2013.

(51) Int. Cl.
*A61B 5/11* (2006.01)
*A61B 5/00* (2006.01)

(56) References Cited

U.S. PATENT DOCUMENTS

| | | | |
|---|---|---|---|
| 4,578,769 | A | 3/1986 | Frederick |
| 4,977,509 | A | 12/1990 | Pitchford et al. |
| 5,058,427 | A | 10/1991 | Brandt |
| 5,224,059 | A | 6/1993 | Nitta et al. |
| 5,295,085 | A | 3/1994 | Hoffacker |
| 5,323,650 | A | 6/1994 | Fullen et al. |
| 5,583,776 | A | 12/1996 | Levi et al. |
| 5,724,265 | A | 3/1998 | Hutchings |
| 5,891,042 | A | 4/1999 | Sham et al. |
| 5,899,963 | A | 5/1999 | Hutchings |
| 5,947,868 | A | 9/1999 | Dugan |
| 5,955,667 | A | 9/1999 | Fyfe |
| 5,976,083 | A | 11/1999 | Richardson et al. |
| 6,018,705 | A | 1/2000 | Gaudet et al. |
| 6,078,874 | A | 6/2000 | Piety et al. |
| 6,145,389 | A | 11/2000 | Ebeling et al. |
| 6,183,425 | B1 | 2/2001 | Whalen et al. |
| 6,204,807 | B1* | 3/2001 | Odagiri ............ G01S 19/34 342/357.57 |
| 6,287,262 | B1 | 9/2001 | Amano et al. |
| 6,301,964 | B1 | 10/2001 | Fyfe et al. |
| 6,305,221 | B1 | 10/2001 | Hutchings |
| 6,309,360 | B1 | 10/2001 | Mault |
| 6,478,736 | B1 | 11/2002 | Mault |
| 6,513,381 | B2 | 2/2003 | Fyfe et al. |
| 6,513,532 | B2 | 2/2003 | Mault et al. |
| 6,529,827 | B1 | 3/2003 | Beason et al. |
| 6,571,200 | B1 | 5/2003 | Mault |
| 6,678,629 | B2 | 1/2004 | Tsuji |
| 6,761,064 | B2 | 7/2004 | Tsuji |
| 6,790,178 | B1 | 9/2004 | Mault et al. |
| 6,813,582 | B2 | 11/2004 | Levi et al. |
| 7,062,225 | B2 | 6/2006 | White |
| 7,162,368 | B2 | 1/2007 | Levi et al. |
| 7,200,517 | B2 | 4/2007 | Darley et al. |
| 7,261,690 | B2 | 8/2007 | Teller et al. |
| 7,457,724 | B2 | 11/2008 | Vock et al. |
| 7,505,865 | B2 | 3/2009 | Ohkubo et al. |
| 7,608,050 | B2 | 10/2009 | Shugg |
| 7,690,556 | B1 | 4/2010 | Kahn et al. |
| 7,774,156 | B2 | 8/2010 | Niva et al. |
| 7,789,802 | B2 | 9/2010 | Lee et al. |
| 7,927,253 | B2 | 4/2011 | Vincent et al. |
| 7,983,876 | B2 | 7/2011 | Vock et al. |
| 8,180,591 | B2 | 5/2012 | Yuen et al. |
| 8,391,888 | B2 | 3/2013 | Hanada et al. |
| 8,684,900 | B2 | 4/2014 | Tran |
| 8,764,651 | B2 | 7/2014 | Tran |
| 9,063,164 | B1 | 6/2015 | Yuen et al. |
| 9,098,991 | B2* | 8/2015 | Park .................. G08B 21/18 |
| 10,132,645 | B1 | 11/2018 | Yuen et al. |
| 2003/0018430 | A1 | 1/2003 | Ladetto et al. |
| 2005/0054938 | A1 | 3/2005 | Wehman et al. |
| 2005/0107723 | A1 | 5/2005 | Wehman et al. |
| 2005/0195830 | A1 | 9/2005 | Chitrapu et al. |
| 2006/0039348 | A1 | 2/2006 | Racz et al. |
| 2006/0047208 | A1 | 3/2006 | Yoon |
| 2007/0050715 | A1 | 3/2007 | Behar |
| 2007/0051369 | A1 | 3/2007 | Choi et al. |
| 2008/0140338 | A1 | 6/2008 | No et al. |
| 2008/0287751 | A1 | 11/2008 | Stivoric et al. |
| 2009/0018797 | A1 | 1/2009 | Kasama et al. |
| 2009/0043531 | A1 | 2/2009 | Kahn et al. |
| 2009/0047645 | A1 | 2/2009 | Dibenedetto et al. |
| 2009/0048044 | A1 | 2/2009 | Oleson et al. |
| 2010/0010774 | A1 | 1/2010 | Ma et al. |
| 2010/0292050 | A1* | 11/2010 | DiBenedetto ............ H04R 3/00 482/9 |
| 2011/0032105 | A1* | 2/2011 | Hoffman ............... G04G 21/025 340/573.1 |
| 2012/0083714 | A1 | 4/2012 | Yuen et al. |
| 2012/0116684 | A1 | 5/2012 | Ingrassia et al. |
| 2012/0179278 | A1 | 7/2012 | Riley et al. |
| 2012/0254934 | A1 | 10/2012 | McBrearty et al. |
| 2012/0283855 | A1 | 11/2012 | Hoffman et al. |
| 2013/0094600 | A1 | 4/2013 | Beziat et al. |
| 2013/0102251 | A1 | 4/2013 | Linde et al. |
| 2013/0274587 | A1* | 10/2013 | Coza .................... A61B 5/6804 600/409 |
| 2014/0180022 | A1 | 6/2014 | Stivoric et al. |
| 2015/0026647 | A1 | 1/2015 | Park et al. |

FOREIGN PATENT DOCUMENTS

| | | |
|---|---|---|
| WO | WO 2012/170924 | 12/2012 |
| WO | WO 2012/171032 | 12/2012 |
| WO | WO 2015/127067 | 8/2015 |
| WO | WO 2016/003269 | 1/2016 |

OTHER PUBLICATIONS

U.S. Office Action dated Aug. 11, 2014, in U.S. Appl. No. 14/050,228.
U.S. Final Office Action dated Dec. 31, 2014, in U.S. Appl. No. 14/050,228.
U.S. Notice of Allowance dated Mar. 17, 2015, in U.S. Appl. No. 14/050,228.
U.S. Office Action dated Dec. 13, 2017, in U.S. Appl. No. 14/713,288.
U.S. Notice of Allowance dated Jul. 13, 2018, in U.S. Appl. No. 14/713,288.
"Activity Classification Using Realistic Data From Wearable Sensors", Parkka, et al, IEEE Transactions on Information Technology in Biomedicine, vol. 10, No. 1, Jan. 2006, pp. 119-128.
"Altimeter and Barometer System", Clifford, et al., Freescale Semiconductor Application Note AN1979, Rev. 3, Nov. 2006.
"Automatic classification of ambulatory movements and evaluation of energy consumptions utilizing accelerometers and barometer", Ohtaki, et al, Microsystem Technologies, vol. 11, No. 8-10, Aug. 2005, pp. 1034-1040.
"Classification of Human Moving Patterns Using Air Pressure and Acceleration", Sagawa, et al, Proceedings of the 24.sup.th Annual Conference of the IEEE Industrial Electronics Society, vol. 2, Aug.-Sep. 1998, pp. 1214-1219.
"Design of a Wireless Assisted Pedestrian Dead Reckoning System—The NavMote Experience", Fang, et al, IEEE Transactions on Instrumentation and Measurement, vol. 54, No. 6, Dec. 2005, pp. 2342-2358.
"Direct Measurement of Human Movement by Accelerometry", Godfrey, et al., Medical Engineering & Physics, vol. 30, 2008, pp. 1364-1386.
"Drift-free dynamic height sensor using MEMS IMU aided by MEMS pressure sensor", Tanigawa, et al, Workshop on Positioning, Navigation and Communication, Mar. 2008, pp. 191-196.
"Evaluation of a New Method of Heading Estimation of Pedestrian Dead Reckoning Using Shoe Mounted Sensors", Stirling et al., Journal of Navigation, vol. 58, 2005, pp. 31-45.
"Fitbit Automatically Tracks Your Fitness and Sleep" published online at web.archive.org/web/20080910224820/http://www.fitbit.com, downloaded Sep. 10, 2008, 1 page.
"Foot Mounted Inertia System for Pedestrian Naviation", Godha et al., Measurement Science and Technology, vol. 19, No. 7, May 2008, pp. 1-9.
"A Hybrid Discriminative/Generative Approach for Modeling Human Activities", Lester, et al., Proc. of the Int'l Joint Conf. Artificial Intelligence, 2005, pp. 766-772.

(56) References Cited

OTHER PUBLICATIONS

"Improvement of Walking Speed Prediction by Accelerometry and Altimetiy, Validated by Satellite Positioning", Perrin, et al, Medical & Biological Engineering & Computing, vol. 38, 2000, pp. 164-168.
"Indoor Navigation with MEMS Sensors", Lammel, et al., Proceedings of the Eurosensors XIII conference, vol. 1, No. 1, Sep. 2009, pp. 532-535.
"An Intelligent Multi-Sensor system for Pedestrian Navigation", Retscher, Journal of Global Positioning Systems, vol. 5, No. 1, 2006, pp. 110-118.
"Non-restricted measurement of walking distance", Sagawa, et al, IEEE Int'l Conf. on Systems, Man, Cybernetics, vol. 3, Oct. 2000, pp. 1847-1852.
"On Foot Navigation: When GPS alone is not Enough", Ladetto, et al, Journal of Navigation, vol. 53, No. 2, Sep. 2000, pp. 279-285.
"SCP 1000-D01/D11 Pressure Sensor as Barometer and Altimeter", VTI Technologies Application, Jun. 2006, Note 33.
"Suunto LUMI User Guide", Jun. and Sep. 1997.
"Using MS5534 for altimeters and barometers", Intersema App., Note AN501, Jan. 2006.
"Validated caloric expenditure estimation using a single body-worn sensor", Lester, et al, Proc. of the Int'l Conf. on Ubiquitous Computing, 2009, pp. 225-234.

\* cited by examiner

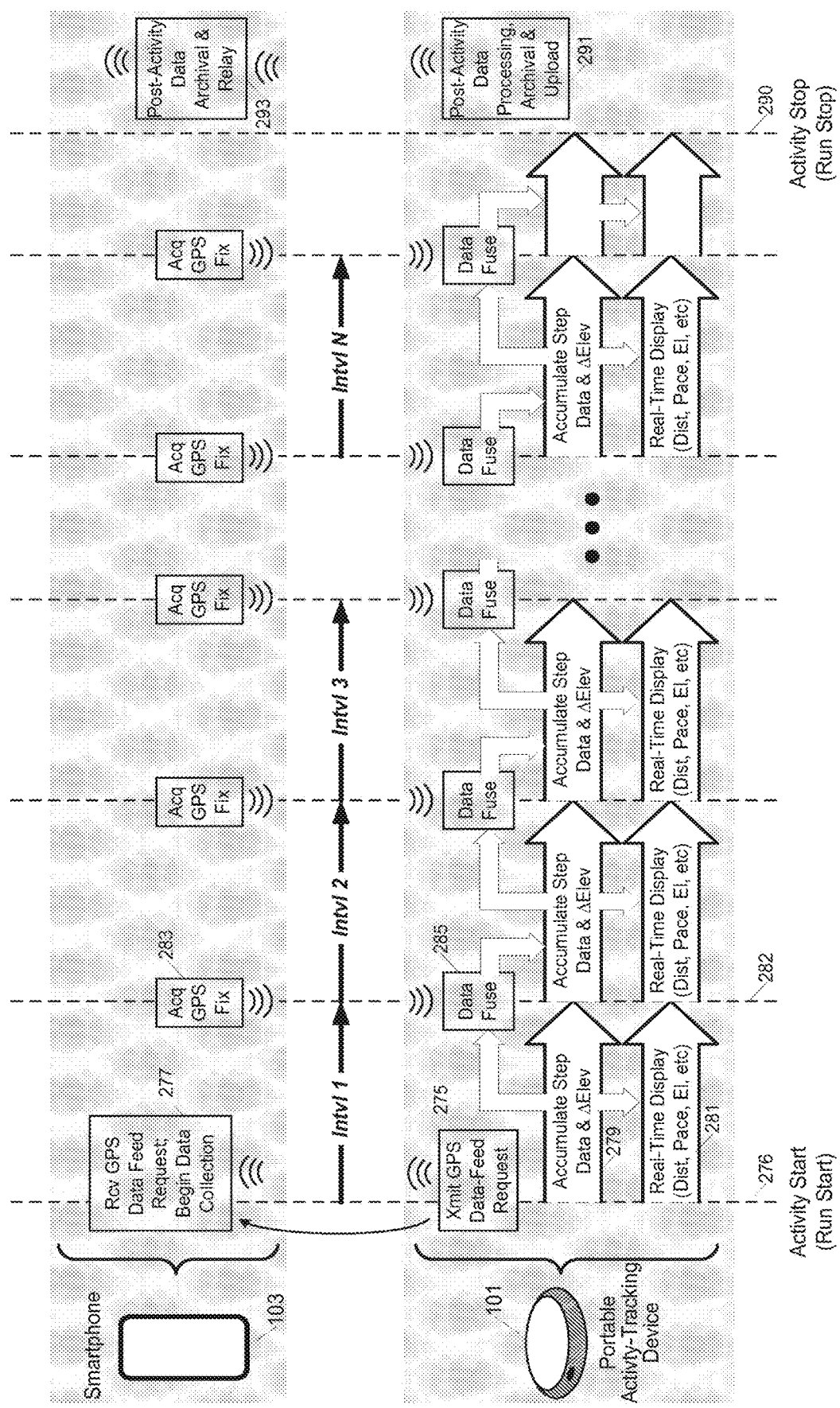

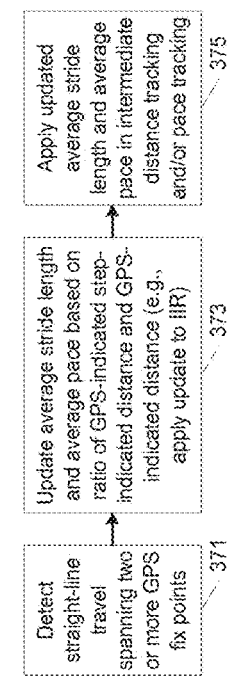
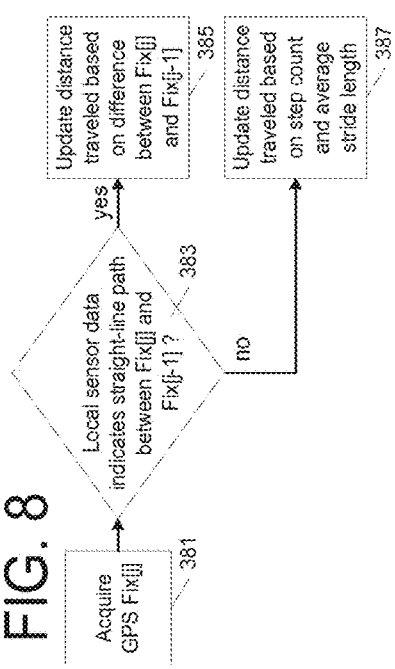
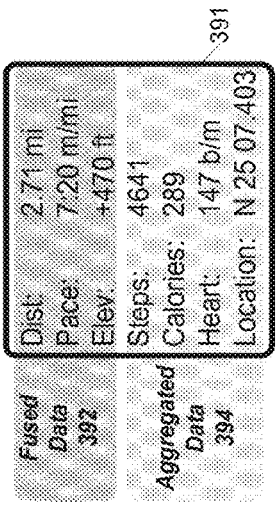
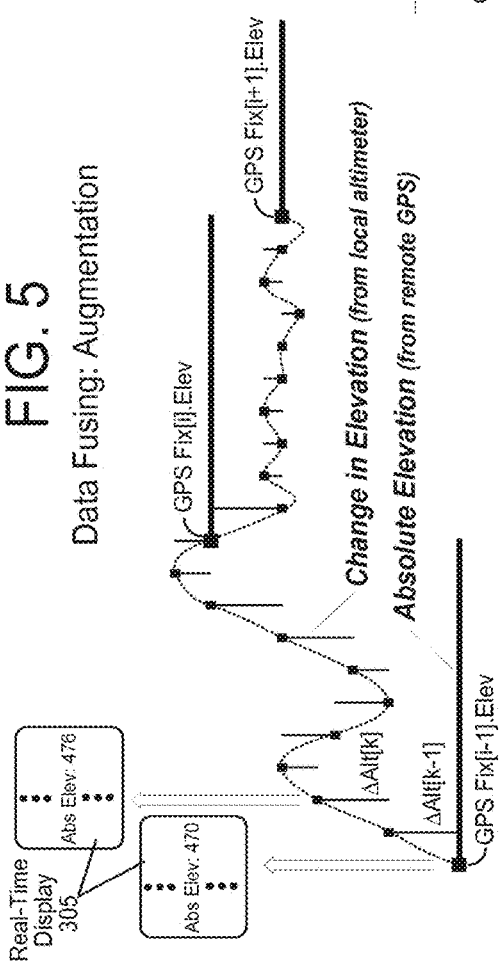
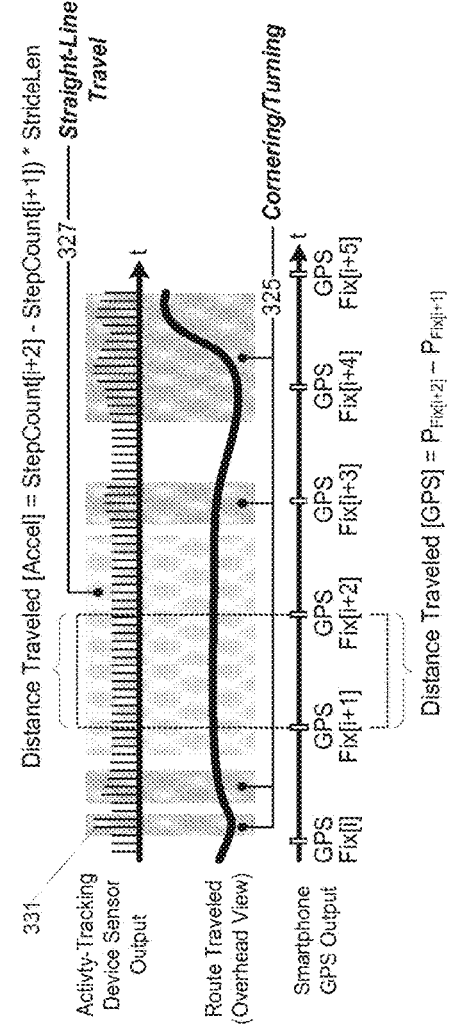

DATA-FUSING ACTIVITY MONITORING DEVICE

TECHNICAL FIELD

The disclosure herein relates to activity monitoring and more particularly to acquiring and displaying activity-related information.

BACKGROUND

Though useful for tracking absolute location and elevation, modern satellite-based positioning devices tend to be bulky and thus unsuited to being worn in view (e.g., as wrist-wear, eye-wear or other visible-at-a-glance accessory) during physically demanding activities such as running or hiking. Also, such devices often fail to provide other types of information desired during physical activity, such as step count, stair-climb count, calorie burn, heart rate, etc.

BRIEF DESCRIPTION OF THE DRAWINGS

The disclosure herein is illustrated by way of example, and not by way of limitation, in the figures of the accompanying drawings and in which like reference numerals refer to similar elements and in which:

FIG. 4 illustrates an example of collaborative activity tracking operation executed by the smartphone and portable activity-tracking device of FIG. 1 in greater detail;

FIG. 5 illustrates an example of a data fusion operation executed within the above-described portable activity-tracking device (or smartphone) with respect to collaboratively collected data;

FIG. 6 illustrates another data fusion example, in this case reconciling discrepancies in collaboratively collected data and dynamically calibrating values used to derive metric data;

FIG. 7 illustrates an example of a dynamic calibration procedure that may be executed within the portable activity-tracking device to revise (calibrate) a user's stride length based on incoming GPS data;

FIG. 8 illustrates an exemplary travel distance calculation obtained by fusing GPS data and data acquired from one or more sensors within the portable activity-tracking device;

FIG. 9 illustrates an exemplary set of metrics presented in real-time on a display element of the portable activity-tracking device;

DETAILED DESCRIPTION

In various embodiments disclosed herein, a portable activity-tracking device receives activity-related information from a discrete data-collection device throughout an activity tracking or monitoring interval and combines the activity-related information with information obtained from one or more local sensors of the activity-tracking device to produce activity metrics for real-time display. In a number of embodiments, for example, the portable activity-tracking device receives positional information from a discrete global-positioning device throughout the activity tracking or monitoring interval (e.g., while a user is engaged in a physical activity) and combines the positional information with information obtained from one or more local sensors of the activity-tracking device for real-time display. By this arrangement, a relatively bulky global-positioning device (e.g., smartphone having global-positioning sensor/circuitry, stand-alone global-positioning device or any other electronics device having global or local positioning capability) may be carried in-pocket or otherwise borne in a not-readily visible location, while a relatively small and lightweight activity-tracking device presents data collaboratively collected by both devices in a real-time, at-a-glance display.

Figure 1:
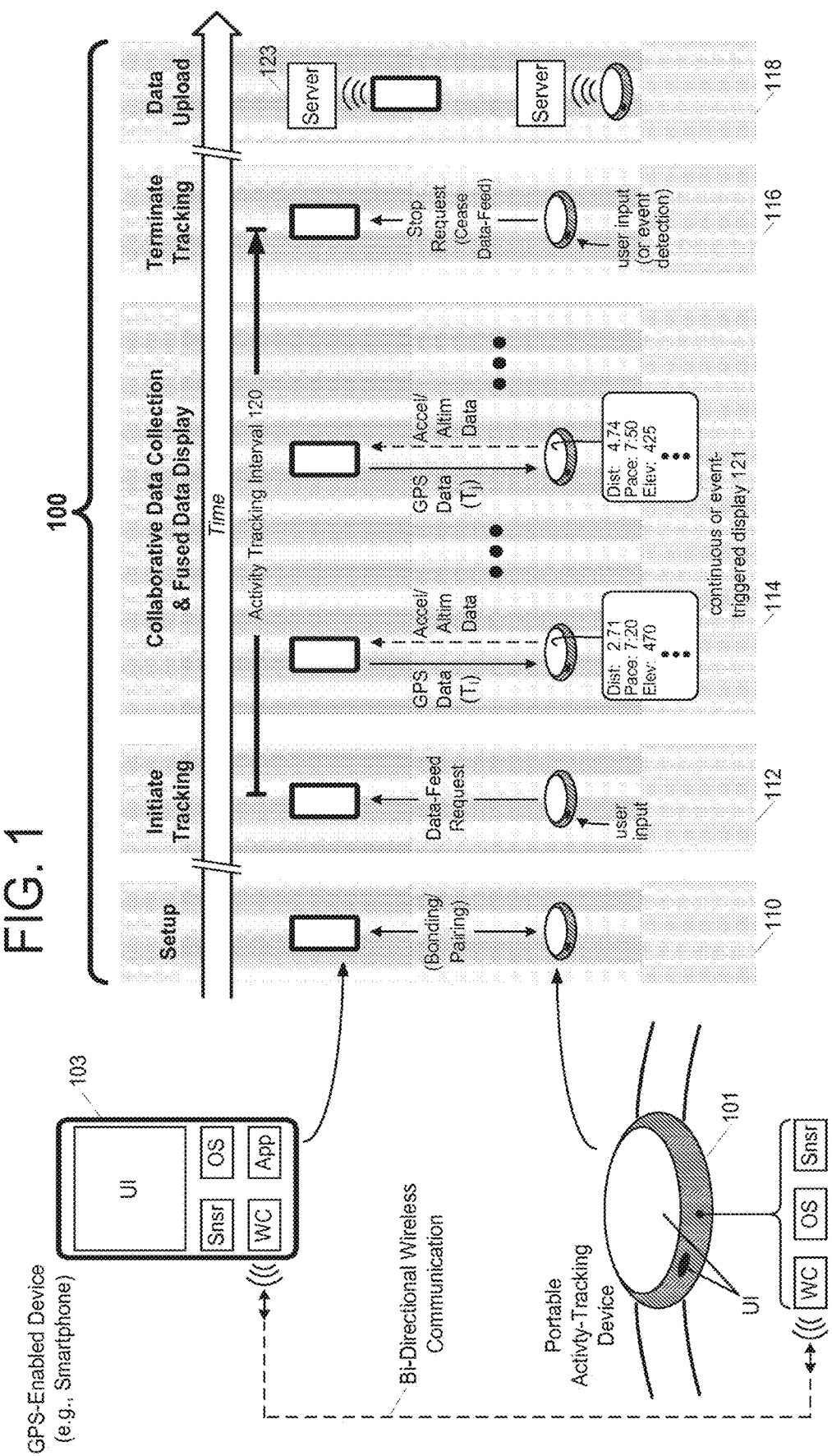
FIG. 1 illustrates an exemplary activity tracking sequence carried out collaboratively by a portable activity-tracking device (also referred to herein as a portable biometric device) and a position-sensing device having GPS (global positioning system) circuitry or other satellite-based or ground-based global positioning capability.

FIG. 1 illustrates an exemplary activity tracking sequence 100 carried out collaboratively by a portable activity-tracking device 101 (also referred to herein as a portable biometric device or portable activity-monitoring device) and a position-sensing device 103 having GPS (global positioning system) circuitry or other satellite-based or ground-based global positioning capability. For purposes of example only, the portable activity-tracking device is assumed to be a wrist-worn device that may be viewed at a glance during physical activity of a user/wearer, while the position-sensing device 103 is assumed to be a GPS-enabled smartphone that the user may carry in his/her pocket, or strap to upper arm or otherwise be borne by the user in a convenient, but not necessarily visible-at-a-glance disposition. In alternative embodiments, position-sensing device 103 may be a stand-alone global positioning device or any other user-location-sensing element. Similarly, instead of being worn on the user's wrist, portable-activity tracking device 101 may be worn or carried in-hand, elsewhere in a readily viewable location on the lower or upper arm, or as eye-wear or other head-up type of display. More generally, portable activity-tracking device 101 may have any form factor and manner of user-bearing (transport or carriage) practical for use during the activity or activities for which it is designed, including attachment mechanisms for attaching to user equipment such as a bicycle, backpack, etc.

Conceptually, portable activity-tracking device 101 may be viewed as having processing circuitry (processor, memory, etc.) to implement an operating system (OS), sensor circuitry (Snsr) and wireless communication circuitry (WC), together with a user interface (UI) having a display and tactile input (e.g., one or more buttons, touch-screen, etc.), though one or more sensors within the sensor circuitry may be used to detect gesture input from the user as discussed below and thus constitute part of the user interface. Portable activity-tracking device 101 may also have an interface to enable wired communication (e.g., a universal serial bus port or other wire interface port). In general, the operating system executes actions in response to input received from the user interface (i.e., user input), sensor circuitry and/or communication circuitry, and presents activity metrics (i.e., information relating to a user activity such as distance traveled, step count, pace of travel, elevation, stairs climbed, calories burned, heart rate, position/location, activity duration and so forth).

As shown, smartphone 103 (or other positioning device) is assumed to have a resident operating system (OS) and activity-tracking/logging app (app), both instantiated by program code execution within a processor (i.e., though not specifically shown, the smartphone includes one or more processors and memory interconnected to form a computing device). Smartphone 103 also includes wireless communication circuitry (WC) for communicating information to the portable activity-tracking device, and position-sensing circuitry (Snsr) such as receiver circuitry for receiving distance and timestamp information from orbiting satellites (e.g., GPS space vehicles within line of sight at any given time).

As FIG. 1 illustrates, operations involved in collaborative activity tracking via GPS-enabled smartphone 103 and portable activity-tracking device 101 (and eventual data archival) may be carried out in phases, including a setup phase 110, initiate-tracking phase 112, collaborative data collection phase 114, terminate-tracking phase 116 and an optional data upload phase 118. In setup phase 110 (i.e., prior to the actual activity tracking interval as shown at 120), position-sensing device 103 and activity-tracking device 101 communicate with one another wirelessly to confirm a trust relationship, thus pairing or bonding to enable collaborative activity tracking at a later point in time. As discussed below, device pairing or bonding may be carried out through user-verification input to each of the two devices (e.g., tactile input, including code or ID entry), or may leverage pre-existing trust relationships with another entity, such as a server computer in which both devices are registered to a given user account or otherwise associated with a user or one another.

In initiate-tracking phase 112, user input to portable activity-tracking device 101 such as a button push, touchscreen tap or predetermined user motion (i.e., a "gesture" detected by one or more sensors within the activity-tracking device) triggers wireless transmission of a data-feed request from activity-tracking device 101 to smartphone 103. In one embodiment, the data-feed request is received via the smartphone's wireless circuitry and forwarded to the smartphone OS which in turn launches an activity-tracking app. The activity-tracking app then interacts with the smartphone OS to request GPS-based position tracking (i.e., regular or intermittent logging of "GPS fix" data, with each such positional fix including, for example and without limitation, a GPS location and time stamp) and wireless transmission of acquired positioning data to activity-tracking device 101. Thereafter, in collaborative data collection phase 114, positioning data captured within smartphone 103 at successive points in time ($T_i$, ..., $T_j$, ...) are transmitted to activity-tracking device 101 to be fused and/or aggregated with data collected from the activity-tracking device's onboard sensors. As shown, the collaboratively collected data (which may be a fusion and/or aggregation of collaboratively collected data) is displayed in real-time continuously or in response to view-gestures (discussed below) on a display 121 of activity-tracking device 103. At the conclusion of the activity being tracked (e.g., walking, running, climbing, riding, swimming, rowing, etc.), which may be explicitly signaled by user input or detected by the collective sensors of the collaborating devices, activity-tracking device 101 issues a stop request to smartphone 103, indicating that positioning-data collection and transmission may be stopped. At some later point in time, collaboratively collected data may be uploaded from activity-tracking device 101 and/or smartphone 103 to a general-purpose computing device (e.g., desktop, laptop, or tablet computer) or server computer 123 for archival and more full-featured rendering (e.g., comparative data display to show differences between activities carried out at different times or by different individuals, depicting route traveled during activity on a geographical map and so forth). For example, activity-tracking device 101 may upload collaboratively collected data to smartphone 103 (e.g., to be logged or archived within activity-tracking/logging app discussed above) and then communicated from smartphone 103 to computing device/server 123.

While the initiate-tracking phase and terminate-tracking phase are depicted in FIG. 1 and described in embodiments below as triggered in response to input to (or event detection within) portable activity-tracking device 101, either or both phases may alternatively be initiated by smartphone/positioning device 103. For example, a user may tap an "initiate-tracking" icon displayed on a touchscreen of smartphone 103 by the above-described smartphone app. The smartphone app may respond to the tap input by transmitting (via the OS and wireless communication circuitry) a "start-tracking" message to portable activity-tracking device 101 and communicate a GPS data collection request to the smartphone OS, relaying collected GPS data to portable activity-tracking device 101 thereafter. Similarly, a stop-tracking icon displayed by the smartphone app may be tapped to trigger communication of a terminate-tracking message to portable activity-tracking device 101 and a cease-OPS-data-collection message to the smartphone OS. More generally, while collected data is generally described as flowing from smartphone 103 (or other positioning device) to portable activity-tracking device 101, data may additionally or alternatively flow from portable activity-tracking device 101 to smartphone 103 before, during and/or after an activity tracking interval 120.

Figure 2:
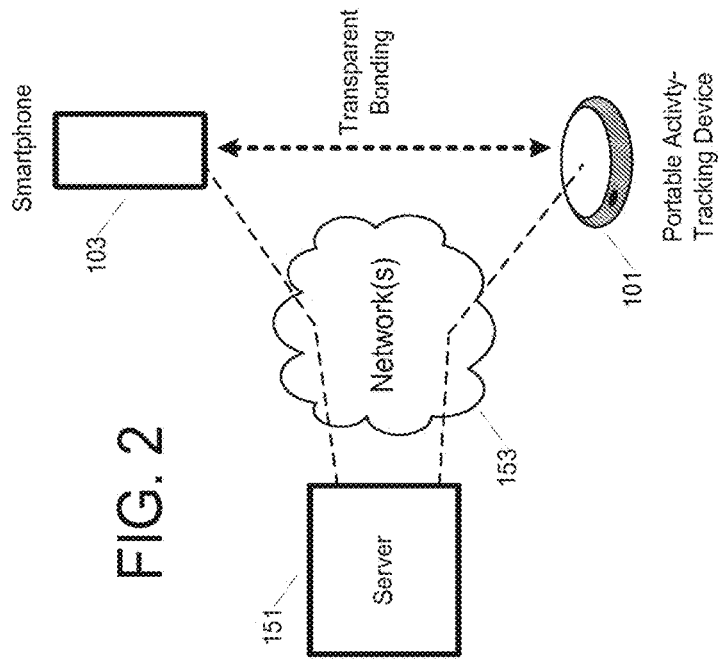

FIGS. 2 and 3 illustrate an exemplary bonding (or more temporary "pairing") of smartphone/positioning-device 103 and portable activity-tracking device 101 and, thus, establishment of a trust relationship in which the devices share collected data with each other. Referring first to FIG. 2, smartphone 103 and portable activity-tracking device 101 are each registered with a network-connected server computer 151 (e.g., a "web" server accessible via the Internet and/or other network(s) 153) and thereby associated with one another by the server. For example, the activity-tracking app on the smartphone may include an interface to enable a user to create an account (i.e., user record) on server 151 and to register the app and/or smartphone as being associated with the user, with a corresponding account credential being supplied to and recorded within the smartphone. The activity-tracking app may further enable the user to identify activity-tracking device 101 (e.g., by entering a registration key or other information) and associate activity-tracking device 101 with the user account, or the activity-tracking device itself may communicate with server 151 via a wired or wireless connection. In either case, activity-tracking device 101 may be associated with the credential, for example, by receiving the credential from server 151. Thereafter, smartphone 103 may automatically (or in response to user input) broadcast a bonding/pairing message bearing the account credential and requesting proximal activity tracking devices associated with the credential to transmit reciprocal bonding/pairing messages. Upon receiving the broadcast bonding/pairing message and confirming association between the activity tracking device's own credential and the credential provided in the bonding/pairing message, portable activity-tracking device 101 responds to the broadcast bonding/pairing message by transmitting a bonding/pairing acknowledgment to the smartphone, together with the activity-tracking device credential to complete the bonding/pairing connection.

Figure 3A:
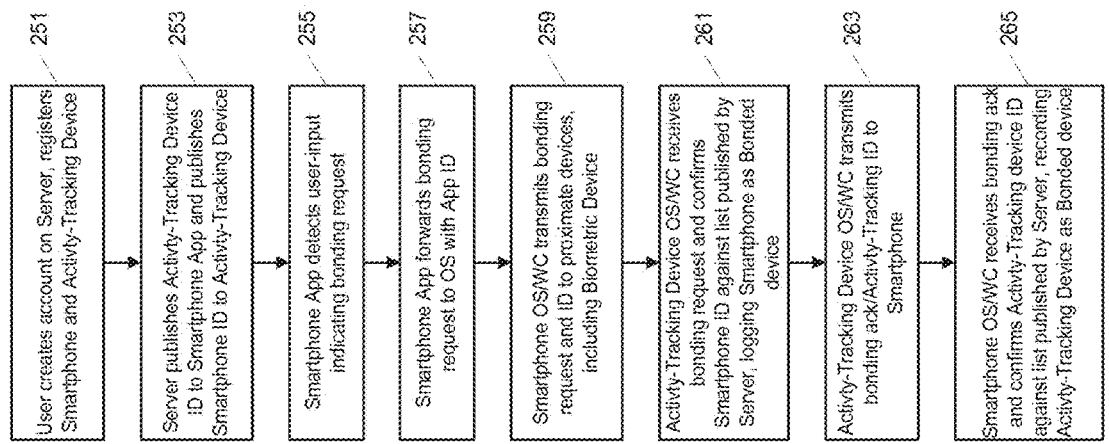
FIGS. 2, 3A and 3B illustrate an exemplary bonding (or more temporary "pairing") of the positioning-device and portable activity-tracking device and thus, establishment of a trust relationship in which the devices share collected data with each other.

FIG. 3A illustrates an exemplary sequence of operations executed to carry out the above-described transparent bonding operation. At 231, a user creates an account on a server computer (i.e., network-connected computer), and then indicates a desire to pair or bond an activity-tracking device to his/her account at 233. A client app on the smartphone or other positioning device (e.g., the activity tracking/logging app discussed above) receives pairing instructions from the server at 235 and then scans for nearby activity-tracking devices at 237, for example, by evaluating incoming presence-indicating messages or other signals emitted by in-range activity-tracking devices sua sponte or in response to smartphone request.

Continuing with the bonding/pairing example shown in FIG. 3, a user/wearer of an activity-tracking device proves possession of the activity-tracking device through a side-channel as shown at 239 (e.g., by entering a number displayed on the activity-tracking device into the smartphone client app and/or by performing a motion/gesture with the activity-tracking device). At 241 the smartphone client app sends the side-band information to the server together with information identifying the activity-tracking device (i.e., an activity-tracking device ID). The smartphone client app then transmits a message to the activity-tracking device requesting the activity-tracking device to enter bonding/pairing mode (as shown at 245), and the activity-tracking device, upon receiving the bonding request, completes the bonding action as shown at 247, for example, by communicating a bonding acknowledgment to the smartphone. Note that the final bonding communication may be a low-level operation managed by the operating systems of the smartphone and activity-tracking device and thus need not be recorded at the level of the smartphone client app or server.

Figure 3B:
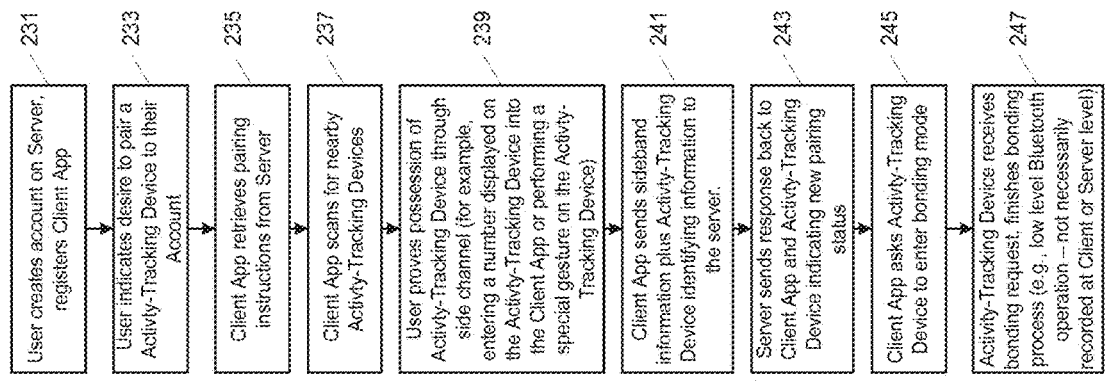

FIG. 3B illustrates an alternative exemplary sequence of operations executed to carry out the above-described transparent bonding operation. At 251, a user creates an account on a server computer (i.e., network connected computer), registering the smartphone and portable activity-tracking device. The server then publishes an identifier (ID) of the portable activity-tracking device to the smartphone at 253 and also publishes an ID of the smartphone of to the portable activity-tracking device. At 255, an application program executed within the smartphone ("smartphone app") detects user input indicating a bonding (or pairing) request and, in response, the smartphone app forwards the bonding request to the OS together with the smartphone ID at 257. The smartphone OS broadcasts the bonding request and ID via the wireless communication circuitry at 259 (e.g., radio communication circuitry in accordance with any of various standards such as Bluetooth, Near-field communication, WiFi, WiMax, etc.) and the activity-tracking device receives the broadcast at 261. As shown, the activity-tracking device confirms the smartphone ID against a list published by the server, logging the smartphone as a trusted, bonded device. At 263 the activity-tracking device transmits a bonding acknowledgment message to the smartphone, the acknowledgement message including the activity-tracking device ID. The smartphone receives the acknowledgment message at 265 and confirms the activity-tracking device ID against the list published by the server, recording the activity-tracking device as a trusted, bonded device and thereby completing the transparent bonding operation.

FIG. 4 illustrates an example of a collaborative activity tracking operation executed by the smartphone/positioning device 103 and portable activity-tracking device 101 of FIG. 1 in greater detail. Assuming the two devices to have been previously bonded (or paired) and that user input or other event detection signals the start of a user activity at 276 (e.g., the user is starting a run or jog), activity-tracking device 101 transmits a GPS data-feed request to smartphone 103 as shown at 275. The smartphone receives the GPS data-feed request at 277 and begins data collection, acquiring a GPS positional fix ("GPS fix") at the conclusion of each of a sequence of uniform or time-varying intervals (lntvl 1, Intvl 2, . . . ) and wirelessly transmitting the GPS fix to the portable activity-tracking device as shown at 283. Note that, though not specifically shown, at least one GPS fix may be acquired and transmitted to the portable activity-tracking device in immediate response to the GPS data-feed request.

For its part, the portable activity-tracking device accumulates "local" step-count and elevation data from on-board sensors (e.g., accelerometer and altimeter, respectively) as shown at 279 and fuses and/or aggregates the local data with incoming GPS data from the smartphone ("remote" data) as shown at 285, logging the fused/aggregated data for continuous or event-triggered presentation on a real-time display (281). As shown, the portable activity-tracking device iteratively fuses and displays collaboratively collected data during each GPS collection interval, ceasing upon detecting activity-stop input 290 from the user (or detecting an event that indicates activity cessation). Thereafter, the portable activity-tracking device processes the collaboratively collected data to produce a finalized, post-activity data set at 291 (e.g., generating or refining tallies) and transmits the finalized data set to the smartphone, optionally archiving the data set within on-board flash memory or other storage. Upon receiving the finalized data set from the portable activity-tracking device, the smartphone may post-process and/or archive the data set within its own storage as shown at 293 (e.g., for on-demand user viewing) and may also relay the finalized data set to a server or other computing device for more full-featured rendering as discussed above.

FIG. 5 illustrates an example of a data fusion operation executed within the above-described portable activity-tracking device (or smartphone) with respect to collaboratively collected data. As shown, absolute elevation information included within each GPS fix (i.e., received from the smartphone GPS circuitry/sensor in the example above) is augmented with elevation-change information obtained from an altimeter within the portable activity-tracking device (i.e., local sensor) to synthesize more detailed elevation data than possible with either sensor alone. More specifically, a sequence of altimeter readings (L1Alt[k−1], L1Alt[k], L1Alt[k+1] . . . ) that indicate changes in user elevation (i.e., relative elevation) are added to absolute user elevation specified in the most recent GPS fix (i.e., Fix[i−1.Elev, Fix[i].Elev, Fix[i+1].Elev, . . . ) to produce more accurate and/or resolute elevation than possible from either the GPS sensor or altimeter alone. Note that the GPS elevation fix points may themselves be output from a filter (e.g., an infinite impulse response filter, finite impulse response filter, common filter, or any other noise filter) as GPS elevation readings tend to be relatively noisy. Also any elevation filtering may be based on information from both local and remote sensors (e.g., altimeter output of activity tracking device and GPS elevation data) and/or may be compensated by topological data indexed based on global positioning coordinates. In any case, an absolute elevation of the user that includes contributions from both the activity-tracking-device altimeter (e.g., a pressure based sensor and/or gyroscope) and the smartphone GPS data may be displayed in real-time on a display 305 of the activity-tracking device.

FIG. 6 illustrates another data fusion example, in this case reconciling discrepancies in collaboratively collected data and dynamically calibrating values used to derive metric data. In the example presented, positional data (i.e., GPS fixes) are assumed to be relatively infrequent relative to a user's stride rate. That is, the user takes multiple (e.g., five, ten or more) strides/steps between successive GPS fix points and thus may round corners or turns that differentiate the actual distance traveled by the user from the distance between GPS fix points. Thus, referring to the overhead view of a route traveled by a runner (or walker), it can be seen that the runner makes several turns (shown in regions 325) which lengthen the distance traveled relative to the Pythagorean distance between any two GPS fix points. Accordingly, a travel distance calculated based on an average stride length and number of strides taken between any two GPS fix points (i.e., step count[i]–step count [i−1] *StrideLen) will, absent other sources of error, be different from the travel distance indicated by those GPS fix points. While this problem may be avoided by increasing the GPS acquisition rate (i.e., to a frequency sufficient that corner rounding may be neglected), it may in some cases or applications to maintain the relatively low GPS acquisition rate (e.g., for power savings) and/or regular GPS fixes may not be available (e.g., in case of travel in an "urban canyon" between large buildings or otherwise obstructed travel path). In those cases, local sensors within the portable activity-tracking device may be used to distinguish cornering/turning from straight-line travel (e.g., using stereo accelerometers, gyro, compass, etc.) and thus enable selection of GPS points acquired along known straight-line travel paths (e.g., as shown at 327) for augmented travel-distance measurement and stride-length calibration. In the example shown, the sensor output of the activity-tracking device (which may include merged data from two or more local sensors as mentioned) includes an acceleration spike 331 for each step taken, together with a lower frequency amplitude variation that increases during cornering maneuvers and decreases during straight line travel. The activity-tracking device may thus apply incoming sensor data (which may be a tuple or vector containing data from multiple sensors) against one or more thresholds to identify straight line travel paths.

FIG. 7 illustrates an example of a dynamic calibration procedure that may be executed within the portable activity-tracking device to revise (calibrate) a user's stride length based on incoming GPS data. Starting at 371, upon detecting a straight line travel path spanning two or more GPS fix points, the portable activity-tracking device calculates the distance traveled over the straight-line path based on both step count (multiplied by average stride length) and GPS positional offsets at 373 (Pythagorean distance between the two or more GPS fix points) and at 375 updates the average stride length (and optionally the average pace) based on the ratio of the OPS-indicated distance and the step-indicated distance. As shown, the newly calculated average stride length update may be input to a filter (e.g., an infinite impulse response filter) to avoid abrupt changes and dithering in average stride length.

FIG. 8 illustrates an exemplary travel distance calculation obtained by fusing GPS data and data acquired from one or more sensors within the portable activity-tracking device. At 381, the portable activity-tracking device acquires an updated GPS fix (GPS Fix[j]). At 383, the portable activity-tracking device evaluates local sensor data at to determine if the sensor data indicates straight-line travel between the newly acquired GPS fix and the immediately prior GPS fix point (i.e., GPS Fix[j] and GPS Fix[j−1]). If so, then the Pythagorean distance between the GPS fix points is used to update the total distance traveled by the user at 385. Otherwise, if the sensor data does not indicate straight-line travel between the most recently acquired GPS fix points, the net travel distance is updated based on the product of the average stride length and step count between the two GPS fix points as shown at 387.

FIG. 9 illustrates an exemplary set of metrics presented in real-time on a display element 391 of a portable activity-tracking device. As shown, the displayed metrics may be categorized as fused data metrics 392 that include contributions from local and remote sensors (e.g., activity-tracking device accelerometer and smartphone GPS circuitry), and aggregated data metrics 394 that are generated based on either local sensor data or remote sensor data, but not both. Thus, distance, pace and elevation may be generated based on fused data (e.g., as discussed above), while step count, calorie burn and heart rate may be generated based exclusively on activity-tracking device sensor information and, conversely, global position ("Location") may be based exclusively on one or more GPS fix points received from the smartphone. Numerous other metrics may be presented based on fused and/or aggregated data in alternative embodiments.

Figure 10:
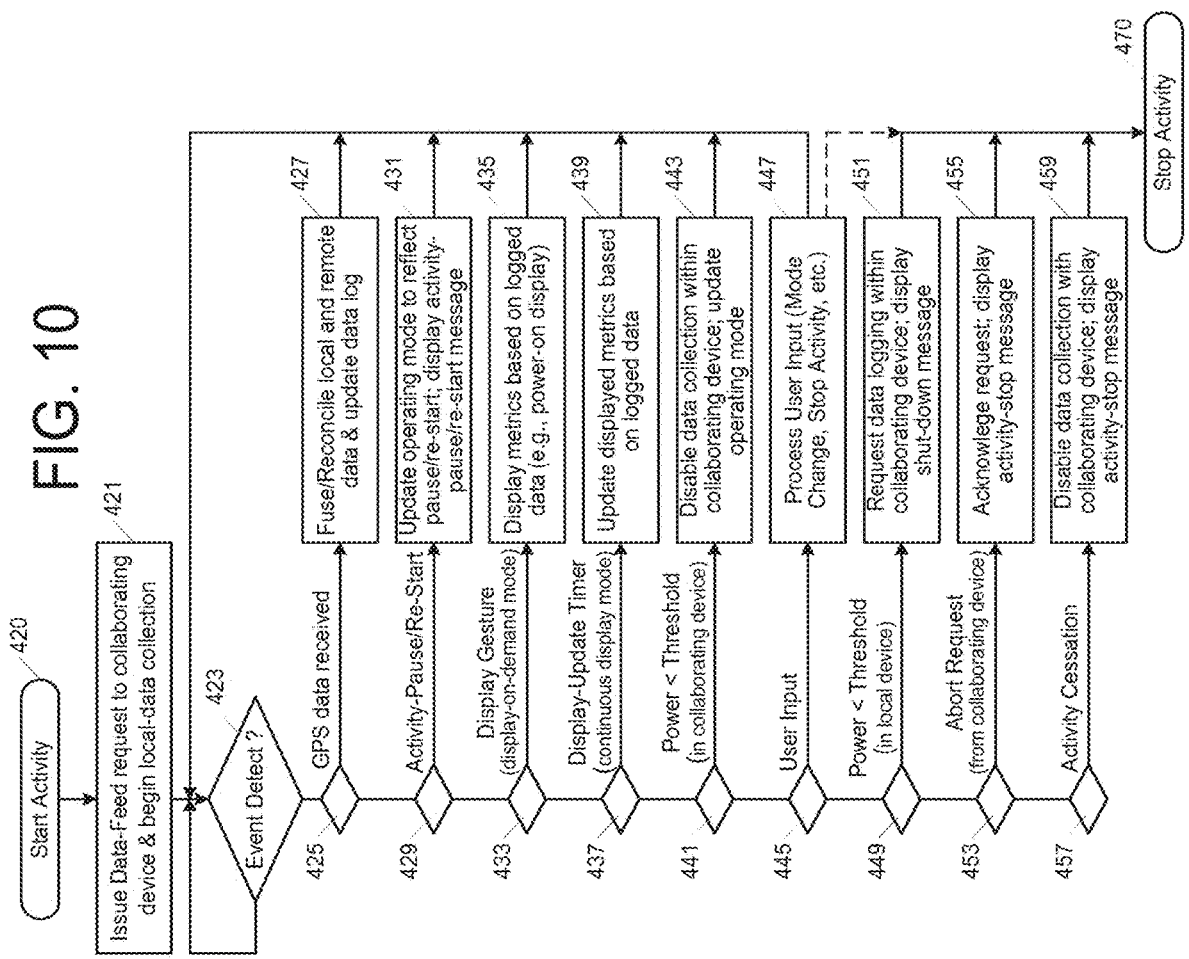
FIG. 10 illustrates an exemplary event loop that may be executed within the portable activity-tracking device during an activity tracking interval.

FIG. 10 illustrates an exemplary event loop that may be executed within the portable activity-tracking device during an activity tracking interval. That is, following an activity-start indication (420) and after issuing or receiving a data-feed instruction 421 to/from the collaborating device (e.g., from portable-activity tracking device to smartphone or other positioning device or vice-versa), the portable activity-tracking device begins logging data obtained from local sensors as described above and responding to events detected at 423. For example, upon detection of incoming GPS data at 425, the portable activity-tracking device fuses (and/or reconciles and/or aggregates) the local and remote data as shown at 427 and stores the result in a data log (i.e., a database of metrics to be occasionally or continuously rendered onto the real-time display of the portable activity-tracking device).

Continuing with the various events that may be detected, if the portable activity-tracking device determines that the activity has paused at 429 (e.g., based on local and/or remote sensor data and/or user-input), the device may update an internally maintained operating mode to reflect the pause event as shown at 431 and may also display an activity-pause message to the user. Similarly, if in an activity-pause mode, sensor input and/or user-input indicating that the activity being tracked has re-started may trigger a converse update to the operating mode (switching back from activity-pause mode to activity-tracking mode) and corresponding re-start message display.

In one embodiment, the portable activity-tracking device is capable of operating in a low-power "display-on-demand" mode in which the display is disabled pending user-input indicating a desire to view activity-tracking metrics. For example, when operating in such a mode, a forearm-raising "view gesture" (e.g., raising a wrist-worn device to viewable height and orientation) may be sensed by an accelerometer and/or other local sensors of the portable activity-tracking device as shown at 433 and used to trigger power-up of the device display, thereby displaying logged activity-tracking metrics to the user in response to the view gesture (435). Though not specifically shown, a countervailing gesture (e.g., lowering the forearm) may be used to disable the display and thus preserve battery power.

In a continuous display mode, the displayed metrics may be updated as shown at 439 (i.e., based on logged data) in response to detecting expiration of an interval timer at 437.

For example, the display may be updated every 60 milliseconds or so and thus continuously from a user's perspective.

Still referring to FIG. 10, if power within the collaborating device is determined to fall below a threshold as shown at 441 (including a zero-power threshold at which the collaborating device simply shuts off), the portable activity-tracking device may disable data collection within the collaborating device (443) and update its internal operating mode to track user activity according to local sensor input only and thus potentially according to different tracking algorithms or heuristics.

Upon detecting user input at 445, the portable activity-tracking device processes the user input and takes responsive action at 447, including stopping activity tracking at 470, changing tracking mode, display mode, etc. Where the user input indicates that activity tracking is to continue without further collaborative data collection, the portable activity-tracking device may send a message to the collaborating device instructing that further data collection may be suspended.

If the power threshold of the portable activity-tracking device is itself determined to fall below a programmed or otherwise predetermined threshold (affirmative determination at 449), the local device may transmit a message to the collaborative device instructing that device to proceed with data logging as shown at 451 (including logging data that had been omitted in view of counterpart data logging within the portable activity-tracking device) and then display a shutdown message to the user.

If the portable-activity tracking device receives an abort message from the collaborating device indicating that activity-tracking is to be aborted (453), the portable activity-tracking device may transmit an acknowledgment to the collaborating device as shown at 455 and display an activity-stop message to the user.

Similarly, if the portable activity-tracking device detects (e.g., via sensor input or otherwise) that the activity being tracked has ceased as shown at 457 (i.e., paused for a threshold period of time), the portable activity-tracking device may transmit a message to the collaborating device to disable data collection and/or transmission therein and may also display an activity-stop message (459).

Figure 11:
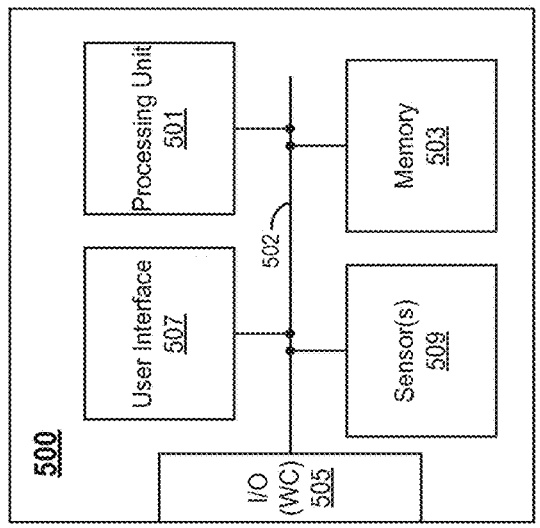
FIG. 11 illustrates a generalized embodiment of a portable activity-tracking device capable of executing the various collaborative activity-tracking and fused-data display operations described above.

FIG. 11 illustrates a generalized embodiment of a portable activity-tracking device 500 capable of executing the various collaborative activity-tracking and fused-data display operations described above. As shown, portable activity-tracking device 500 includes a processing unit 501, memory 503 for storing program code executed by the processing unit to effect the various methods and techniques of the above-described embodiments. Note that the processing unit itself may be implemented by a general or special purpose processor (or set of processing cores) and thus may execute sequences of programmed instructions to effectuate the various activity-tracking operations described above (including related setup and data upload phases).

Still referring to FIG. 11, activity-tracking device 500 further includes one or more sensors 509 as described above (e.g., accelerometer, altimeter, compass, gyroscope, heart-rate monitor, temperature sensor, optical or auditory sensors and so forth), input/output (I/O) ports 505 for receiving and outputting data (including wireless communication circuitry as described above), and a user interface 507 having, for example and display and tactile user-input elements (touchscreen, buttons, etc.) to enable a user to control operation of the activity-tracking device as described above. Though not shown, numerous other functional blocks may be provided within activity-tracking device 500 according to specialized functions intended to be carried out by the device and/or intended operating environment. Further, the functional blocks within activity-tracking device 500 are depicted as being coupled by a communication path 502 which may include any number of shared or dedicated buses or signaling links. More generally, the functional blocks shown may be interconnected in a variety of different architectures and individually implemented by a variety of different underlying technologies and architectures. With regard to the memory architecture, for example, multiple different classes of storage may be provided within memory 503 to store different classes of data. For example, memory 503 may include non-volatile storage media such as fixed or removable semiconductor-based storage media to store executable code and related data, volatile storage media such as static or dynamic RAM and so forth.

The various activity-tracking data structures, methods and techniques disclosed herein may be implemented through execution of one or more sequences of instructions (i.e., software program(s)) within a computer system, or by a custom-built hardware ASIC (application-specific integrated circuit), or programmed on a programmable hardware device such as an FPGA (field-programmable gate array), or any combination thereof within or external to the computer system.

When received within a computer system via one or more computer-readable media, such data and/or instruction-based expressions of the above described circuits and functional blocks can be processed by a processing entity (e.g., one or more processors) within the computer system in conjunction with execution of one or more other computer programs including, without limitation, net-list generation programs, place and route programs and the like, to generate a representation or image of a physical manifestation of such circuits. Such representation or image can thereafter be used in device fabrication, for example, by enabling generation of one or more masks that are used to form various components of the circuits in a device fabrication process.

In the foregoing description and in the accompanying drawings, specific terminology and drawing symbols have been set forth to provide a thorough understanding of the disclosed embodiments. In some instances, the terminology and symbols may imply specific details that are not required to practice those embodiments. For example, any of the specific dimensions, form factors, signal path widths, signaling or operating frequencies, component circuits or devices and the like can be different from those described above in alternative embodiments. Additionally, links or other interconnection between system components or internal circuit elements or blocks may be shown as buses or as single signal lines. Each of the buses can alternatively be a single signal line, and each of the single signal lines can alternatively be buses. Signals and signaling links, however shown or described, can be single-ended or differential. A signal driving circuit is said to "output" a signal to a signal receiving circuit when the signal driving circuit asserts (or de-asserts, if explicitly stated or indicated by context) the signal on a signal line coupled between the signal driving and signal receiving circuits. The term "coupled" is used herein to express a direct connection as well as a connection through one or more intervening circuits or structures. Device "programming" can include, for example and without limitation, loading a control value into a register or other storage circuit within the integrated circuit device in response to a host instruction (and thus controlling an operational aspect of the device and/or establishing a device configuration) or through a one-time programming operation (e.g., blowing fuses within a configuration circuit during device production), and/or connecting one or more selected pins or other contact structures of the device to reference voltage lines (also referred to as strapping) to establish a particular device configuration or operation aspect of the device. The terms "exemplary" and "embodiment" are used to express an example, not a preference or requirement. Also, the terms "may" and "can" are used interchangeably to denote optional (permissible) subject matter. The absence of either term should not be construed as meaning that a given feature or technique is required.

Various modifications and changes can be made to the embodiments presented herein without departing from the broader spirit and scope of the disclosure. For example, features or aspects of any of the embodiments can be applied in combination with any other of the embodiments or in place of counterpart features or aspects thereof. Accordingly, the specification and drawings are to be regarded in an illustrative rather than a restrictive sense.

What is claimed is:

1. A method of operating an activity monitoring device, the method comprising:
    obtaining change in elevation data from one or more sensors of the activity monitoring device of a user associated with the activity monitoring device;
    wirelessly receiving absolute elevation information from a discrete global-positioning device for a sequence of points traveled by the user;
    augmenting the absolute elevation information from the discrete global-positioning device and the change in elevation data from the activity monitoring device to calculate an absolute elevation of the user; and
    causing the user absolute elevation to be displayed on a display of the activity monitoring device.

2. The method of claim 1, wherein augmenting the absolute elevation information includes updating the absolute elevation information with the change in elevation data across a sequence of readings from the one or more sensors.

3. The method of claim 1, wherein the one or more sensors include one or more altimeters.

4. The method of claim 1, further comprising:
    obtaining a step count of the user from one or more accelerometers of the activity monitoring device;
    wirelessly receiving positioning data of the user from the discrete global-positioning device; and
    causing aggregated data metrics to be displayed on the display of the activity monitoring device, wherein the aggregated data metrics include contributions from either the step count or the positioning data.

5. The method of claim 4, further comprising:
    calculating a distance traveled or pace of travel based at least in part on the positioning data from the discrete global-positioning device and based at least in part on the step count from the activity monitoring device; and
    causing fused data metrics to be displayed on the display of the activity monitoring device, wherein the fused data metrics include contributions from both the step count and the positioning data.

6. The method of claim 1, further comprising:
    receiving an instruction to monitor activity of the user; and
    causing the discrete global-positioning device to transmit the absolute elevation information to the activity monitoring device in response to receiving the instruction to monitor activity of the user.

* * * * *